US011157647B2

(12) United States Patent
Yang et al.

(10) Patent No.: US 11,157,647 B2
(45) Date of Patent: Oct. 26, 2021

(54) ACCESS SYSTEM, ACCESS DEVICE AND ACCESS METHOD FOR ACCESSING HEALTH INFORMATION (71) Applicant: Industrial Technology Research Institute, Hsinchu (TW)

(72) Inventors: Cheng-Yi Yang, Hsinchu (TW); Yu-Chieh Pan, Hsinchu (TW); Hsing-Chen Lin, Hsinchu (TW)

(73) Assignee: Industrial Technology Research Institute, Hsinchu (TW)

( * ) Notice: Subject to any disclaimer, the term of this patent is extended or adjusted under 35 U.S.C. 154(b) by 358 days.

(21) Appl. No.: 16/232,436

(22) Filed: Dec. 26, 2018

(65) Prior Publication Data
US 2020/0184099 A1 Jun. 11, 2020

(30) Foreign Application Priority Data
Dec. 6, 2018 (TW) ................. 107143825

(51) Int. Cl.
*G06F 21/60* (2013.01)
*G06F 21/62* (2013.01)
(Continued)

(52) U.S. Cl.
CPC .......... *G06F 21/6245* (2013.01); *G06F 16/13* (2019.01); *G06F 21/602* (2013.01);
(Continued)

(58) Field of Classification Search
CPC .... G06F 21/6245; G06F 21/602; G06F 16/13; G06F 16/9024; H04L 9/30; H04L 9/0637;
(Continued)

(56) References Cited

U.S. PATENT DOCUMENTS 8,725,536 B2\* 5/2014 Deobhakta ............. G06Q 10/10
705/3
10,841,286 B1\* 11/2020 Davidovics ........... H04L 9/3247
(Continued)

FOREIGN PATENT DOCUMENTS

CN 106934243 A 7/2017
CN 107391944 A 11/2017
(Continued)

*Primary Examiner* — Khoi V Le
(74) *Attorney, Agent, or Firm* — Mintz Levin Cohn Ferris Glovsky and Popeo, P.C.; Peter F. Corless; Steven M. Jensen (57) ABSTRACT

An access system, an access device and an access method for accessing health information are disclosed. The access system includes a decentralized database for recording an authorization file corresponding to health information and a public key corresponding to the authorization file, a centralized database for using the public key corresponding to the authorization file to encrypt and store the health information corresponding to the authorization file into an access space, and an access device for issuing an access request of health information to the decentralized database based on user identification, for the decentralized database to identify and authorize the user identification based on the authorization file corresponding to the health information and ratify the access request and provide an instruction after identifying and authorizing the user identification, and for acquiring the encrypted health information from the access space based on the instruction.

20 Claims, 6 Drawing Sheets (51) Int. Cl.
*H04L 9/30* (2006.01)
*G06F 16/13* (2019.01)
*G16H 10/60* (2018.01)
*H04L 9/06* (2006.01)

(52) U.S. Cl.
CPC .......... *G16H 10/60* (2018.01); *H04L 9/0637* (2013.01); *H04L 9/30* (2013.01); *H04L 2209/38* (2013.01)

(58) Field of Classification Search
CPC ... H04L 9/3247; H04L 9/0894; H04L 9/3239; H04L 2209/38; H04L 2209/88; G16H 10/60
See application file for complete search history.

(56) References Cited

U.S. PATENT DOCUMENTS

| | | | |
|---|---|---|---|
| 2015/0213195 A1* | 7/2015 | Blechman | G16H 10/60 705/51 |
| 2016/0292453 A1* | 10/2016 | Patterson | H04L 9/088 |
| 2018/0060496 A1* | 3/2018 | Bulleit | H04L 9/3239 |
| 2018/0121620 A1* | 5/2018 | Bastide | H04W 12/126 |

FOREIGN PATENT DOCUMENTS

| | | |
|---|---|---|
| CN | 107579979 A | 1/2018 |
| CN | 108682445 A | 10/2018 |
| CN | 108881160 A | 11/2018 |
| EP | 3 236 374 A1 | 10/2017 |
| TW | M554608 U | 1/2018 |
| TW | M569002 U | 10/2018 |

\* cited by examiner

FIG. 4 purse/public key registration management — 3a

| purse address (ID) | public key | name/ nickname |
|---|---|---|
| 0x12... | 12921... | Peter |
| 0xb4... | 49873... | John |
| 0xab... | 63195... | OO insurance company |
| 0x63... | 34126... | OO hospital | authorized document signature

| authorized object | start and end time | authorizer + signature |
|---|---|---|
| 0xab... | 2018/01/01 2018/12/31 | 0xb4... |

ACCESS SYSTEM, ACCESS DEVICE AND ACCESS METHOD FOR ACCESSING HEALTH INFORMATION

CROSS REFERENCE TO RELATED APPLICATIONS

The present application is based on, and claims priority from, Taiwan Application Serial Number 107143825, filed on Dec. 6, 2018. The entirety of the above-mentioned patent application is hereby incorporated by reference herein and made a part of this specification.

BACKGROUND

1. Technical Field

This disclosure relates to access systems, access devices and access methods, and, more particularly, to an access system, an access device and an access method for accessing health information.

2. Description of Related Art

Conventionally, personal data authorization mechanisms in health and medical care fields are signed in writing. However, it is difficult to preserve paper and solve disputes when the written agreement is lost. Besides, it is easy to forge a written paper agreement if the agreement is not managed and taken care of by a fair third party. The contents of the paper agreement have to be determined by men, and the data thereof cannot be obtained until the authorization is granted. Therefore, the paper agreement is hard to be processed subsequently by a machine (e.g., a computer).

With the rapid development of insurance technology and computerization of health information and authorization file, personal data of insurance policy holders or patients are likely exchanged among hospitals, health service providers and data analyzers. Therefore, the confidentiality of personal data and the identification of authorization are becoming important. However, the existing technology does not determine if the personal data is still in the authorized period. When a plurality of people are authorized and each person has his own authorization time or authorization content, data will be accessed difficultly. Although personal data, such as health information and case history data, can be uploaded to a block chain to reduce the risk and increase safety, the data on the block chain cannot be deleted and are likely leaked if the private key is lost.

How to address the personal data authorization mechanism that is designed to protect personal data, increase the personal data exchanging efficiency among different entities, and improve the reliability of right-obligation relationship of a contract, and integrate individual data is becoming an urgent issue in the art.

SUMMARY

In order to solve the problems of the prior art, an access system, an access device and an access method for accessing health information are provided.

In an embodiment, an access device for accessing health information according to the present disclosure comprises: an identifier configured for identifying user identification to obtain a private key corresponding to the user identification; a communication apparatus configured for issuing an access request of health information to a decentralized database based on the user identification, for the decentralized database to identify and authorize the user identification based on a recorded authorization file corresponding to the user identification and ratify the access request and provide an instruction after identifying and authorizing the user identification, and for acquiring encrypted health information from a centralized database based on the instruction; and a processor configured for using the private key to decrypt the encrypted health information to obtain the health information.

In another embodiment, an access method for accessing health information according to the present disclosure comprises: identifying user identification to obtain a private key corresponding to the user identification; issuing, based on the user identification, an access request of health information to a decentralized database, for the decentralized database to identify and authorize the user identification based on an authorization file corresponding to the health information and ratify the access request and provide an instruction after identifying and authorizing the user identification; acquiring encrypted health information from an access space of a centralized database based on the instruction; and using the private key to decrypt the encrypted health information to obtain the health information.

In yet another embodiment, an access system for accessing health information according to the present disclosure comprises: a decentralized database configured to recording an authorization file corresponding to health information and a public key corresponding to the authorization file; a centralized database configured to storing health information corresponding to the authorization file, and using a public key corresponding to the authorization file to encrypt and store the health information corresponding to the authorization file into an access space of the centralized database; and an access device configured for issuing an access request to the decentralized database based on user identification, for the decentralized database to identify and authorize the user identification based on the authorization file corresponding to the health information and ratify the access request and provide an instruction after identifying and authorizing the user identification, and for capturing the encrypted health information from the access space based on the instruction.

In still another embodiment, an access method for accessing health information according to the present disclosure comprises: using a public key corresponding to an authorization file and recorded in a decentralized database to encrypt and store health information corresponding to the authorization file and stored in a centralized database into an access space of the centralized database; issuing, by an access device, an access request of the health information to the decentralized database based on user identification; identifying and authorizing the user identification based on the authorization file recorded in the decentralized database and corresponding to the health information, and ratifying the access request and providing an instruction after the user identification is identified and authorized; and acquiring, by the access device, the encrypted health information from the access space based on the instruction.

BRIEF DESCRIPTION OF DRAWINGS

The disclosure can be more fully understood by reading the following detailed description of the preferred embodiments, with reference made to the accompanying drawings, wherein.

DETAILED DESCRIPTION

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

Figure 1:
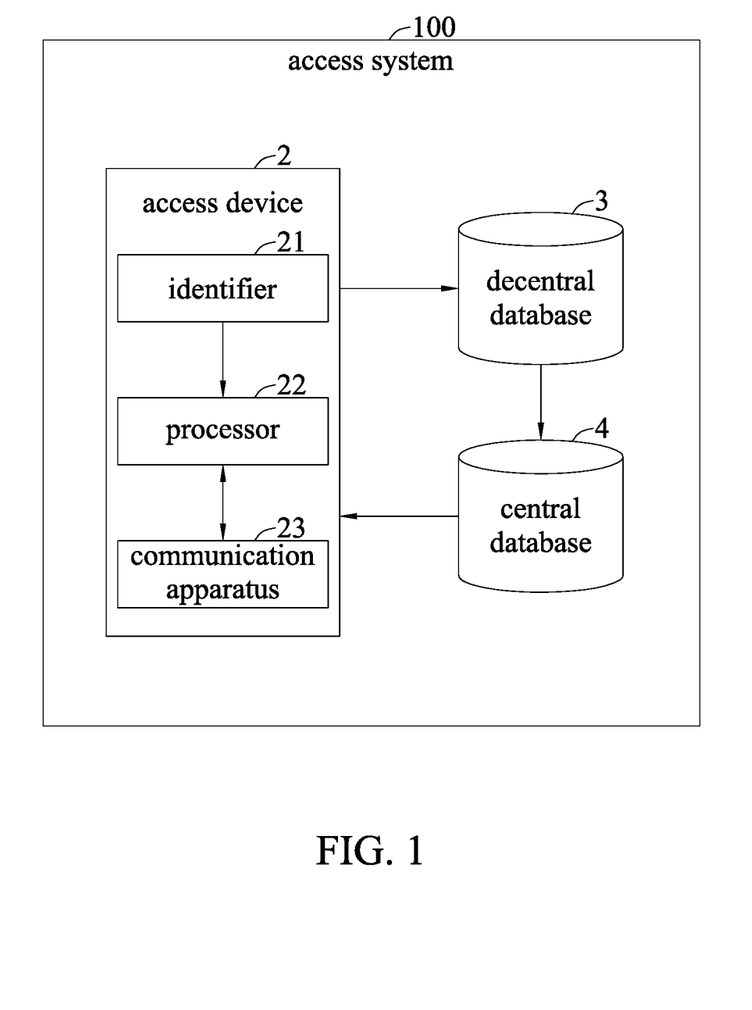
FIG. 1 is a functional block diagram of an access system and an access device for accessing health information of an embodiment according to the present disclosure.

FIG. 1 is a functional block diagram of an access system 100 comprising the access device 2, a decentralized database 3 and a centralized database 4.

The decentralized database 3 records an authorization file corresponding to health information (e.g., a case history record) and a public key corresponding to an authorization object in the authorization file. In an embodiment, the authorization file records an authorization object, authorization time or an authorization content, the case history record includes a case history number and a case history data (e.g., a hospital discharge abstract, out-patient medicines, a surgery report or a medical image report), and the decentralized database 3 is basically a block chain, allowing a patient or an insurance policy holder to sign or change the authorization file corresponding to the health information on the block chain. The decentralized database 3 records the authorization file. The decentralized database 3 does not record the health information, in order to prevent the health information from being leaked due to improper encryption or loss of a private key. Besides, the problems of the prior art that the authorization cannot be revoked and it is hard to amend the authorization content since the health information is stored on the block chain can be solved.

The centralized database 4 uses the public key corresponding to the authorization file recorded in the decentralized database 3 to encrypt the health information corresponding to the authorization file in the centralized database 4 and stores the encrypted health information into an access space (not shown) of the centralized database 4. In an embodiment, the centralized database 4 is a hospital original case history database, which can be a case history database of a hospital, and the access space is a hospital encrypted case history database and has an access address, which can be considered as a temporarily encrypted case history database across hospitals. The centralized database 4 encrypts health information of different patients or insurance policy holders and stores the encrypted health information in the access space temporarily, for the identified and authorized access device 2 to acquire the encrypted health information. In an embodiment, the centralized database 4 searches the decentralized database 3 for an authorization file corresponding to the health information periodically, and encrypts the health information corresponding to the authorization file and stores the encrypted health information into the access space of the centralized database 4 when the authorization file corresponding to the health information is in the decentralized database 3.

The access device 2 comprises an identifier 21, a processor 22 and a communication apparatus 23. The identifier 21 identifies user identification. In an embodiment, the identifier 21 is a reader that receives a chip card or an RFID card and reads a private key of user identification, or is an identification identifier that identifies a fingerprint, palm prints, vein distribution, an iris, a retina, facial features or a signature, to acquire the user identification and transform the user identification into the private key.

The communication apparatus 23 issues an access request of health information to the decentralized database 3 based on the user identification. The decentralized database 3 identifies and authorizes the user identification based on the authorization file corresponding to the health information recorded in the decentralized database 3 by identifying if the user identification, based on which the decentralized database 3 identifies the access device 2, matches an authorization object in the authorization file or identifying if time when the access device 2 issues the access request matches authorization time in the authorization file. After identifying and authorizing the user identification, the decentralized database 3 ratifies the access request and provides an instruction to the access device 2. In an embodiment, the instruction is an access address of the encrypted health information. The communication apparatus 23 acquires the encrypted health information from the access space of the centralized database 4 at the access address based on the instruction. When using the access device 2, patients or insurance policy holders can sign or authorize the authorization file corresponding to the health information on the decentralized database 3 based on the user identification via the communication apparatus 23.

The processor 22 uses the private key corresponding to the user identification to decrypt the encrypted health information to acquire the health information. The access device 2 further comprises a display for displaying the health information decrypted by the processor 22, or a storage apparatus for storing the health information decrypted by the processor 22.

Since each user identification has a pair of corresponding public key and private key, wherein the public key corresponds to an authorization object in an authorization file and recorded in the decentralized database 3 and the private key is acquired by the access device 2 identifying user identification, the centralized database 4 can use the public key in the decentralized database 3 to encrypt health information in the centralized database 4 and stores the encrypted health information in the access space. Therefore, when the decentralized database 3 identifies that the user identification of the access device 2 matches the authorization object in the authorization file and the time when the access request is issued matches the authorization time, the access device 2 can acquire the encrypted health information from the access space of the centralized database 4 based on the instruction, and use the private key to decrypt the encrypted health information.

Figure 2:
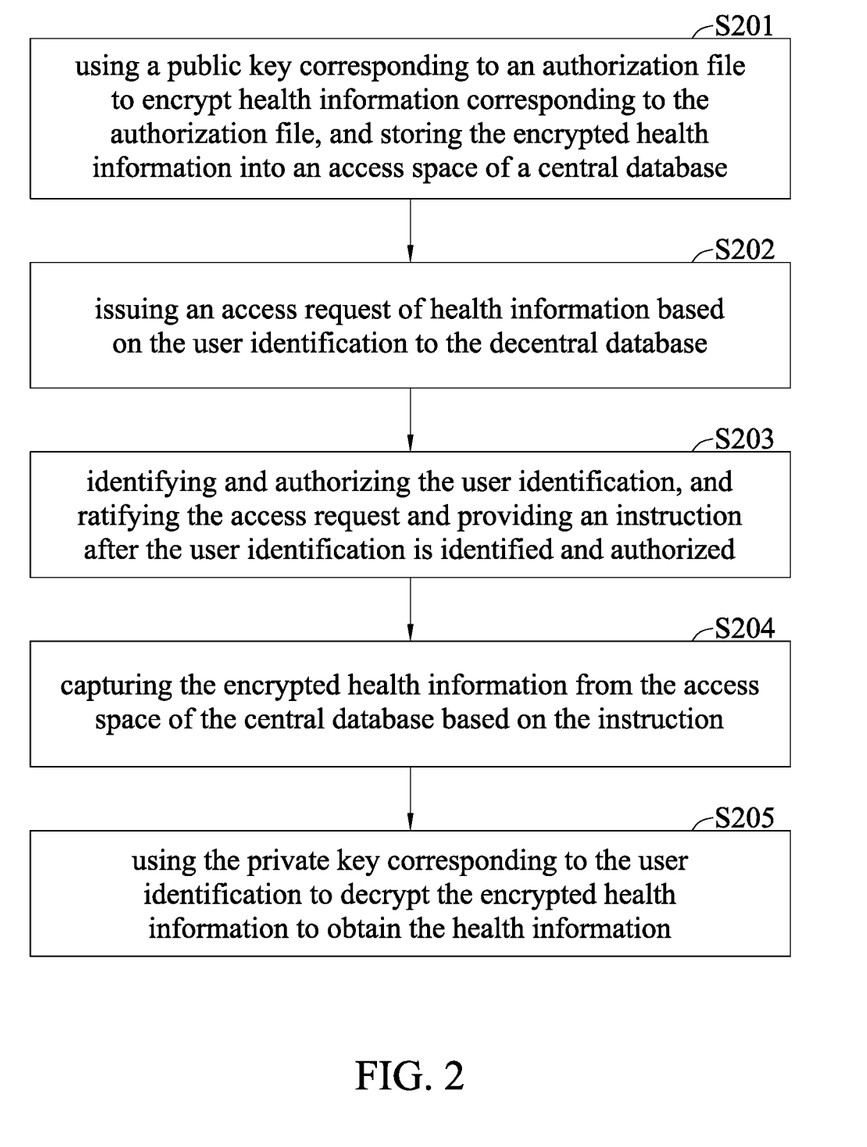
FIG. 2 is a flow chart of an access method for accessing health information of an embodiment according to the present disclosure.

Refer to FIG. 2, which is a flow chart of an access method for accessing health information of an embodiment according to the present disclosure. Steps S201-S204 illustrate the operation of an access system for accessing health information according to the present disclosure.

In step S201, a public key corresponding to an authorization file is used to encrypt health information corresponding to the authorization file, and the encrypted health information is stored into an access space of a centralized database. Step S201 is executed by a centralized database. The authorization file and the public key corresponding to the authorization file are recorded in a decentralized database (e.g., a block chain). The health information corresponding to the authorization file is stored in a centralized database (e.g., a hospital original case history database). The encrypted health information is stored in an access space (e.g., a hospital encrypted case history database).

In step S202, an access request of health information is issued based on the user identification to the decentralized database. Step S202 is executed by the access device. The access device can be a chip card or an RFID card to read or identify biology features, such as a finger print or palm prints, to acquire user identification and a private key corresponding to the user identification.

In step S203, the user identification is identified and authorized, and the access request is ratified and an instruction is provided after the user identification is identified and authorized. Step S203 is executed by the decentralized database. The decentralized database identifies and authorizes the user identification by identifying if the user identification matches the authorization object in the authorization file or if time when the access request is issued matches the authorization time of the authorization file. In an embodiment, the instruction is an access address of the centralized database.

In step S204, the encrypted health information is captured from the access space of the centralized database based on the instruction. Step S204 is executed by the access device.

In step S205, the private key corresponding to the user identification is used to decrypt the encrypted health information to obtain the health information. Step S205 is executed by the access device. The user identification includes a pair of corresponding public key and private key, wherein the public key corresponds to the authorization object in the authorization file and recorded in the decentralized database, and the private key is acquired by the access device identifying the user identification. Therefore, that the user identification is identified and authorized successfully indicates that the user identification of the access device matches the authorization object in the authorization file and the time when the access request is issued also matches the authorization time in the authorization file. Accordingly, the access device can use the private key to decrypt the encrypted health information that is encrypted by the public key.

Figure 3:
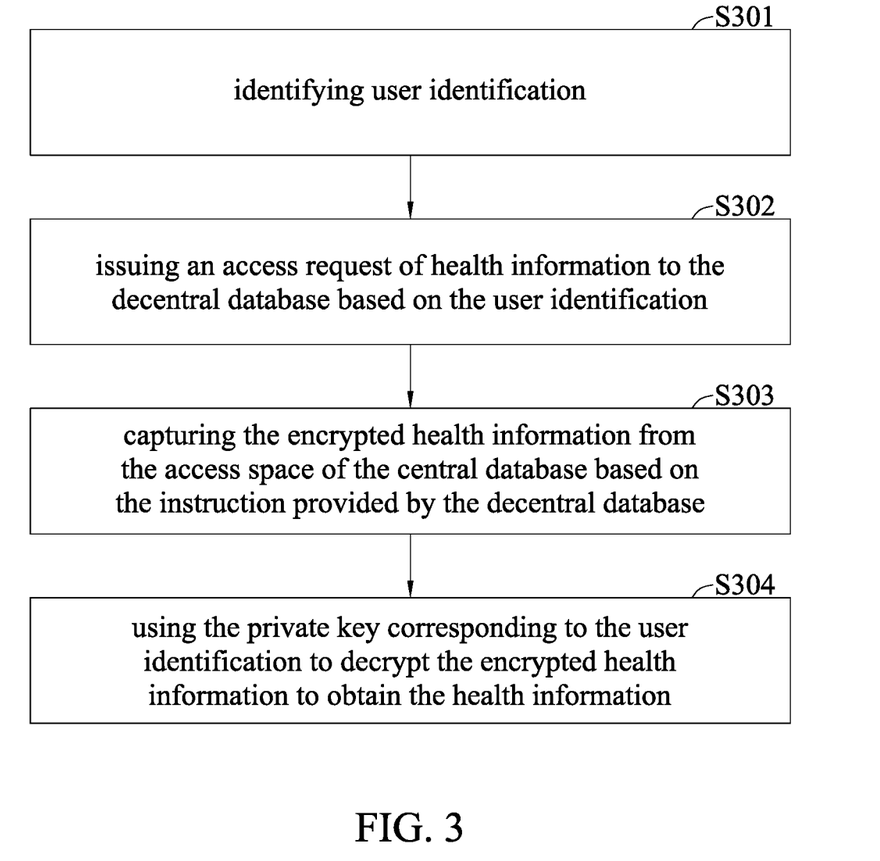
FIG. 3 is a flow chart of an access method for accessing health information of another embodiment according to the present disclosure.

Refer to FIG. 3, which is a flow chart of an access method for accessing health information of another embodiment according to the present disclosure. Steps S301-S304 illustrate the operation of an access system for accessing health information according to the present disclosure. Steps S301-S304 are all executed by the access device.

In step S301, user identification is identified. The access device can receive a chip card or an RFID card to read user identification or identify biology features, such as a finger print or palm prints, to obtain the user identification.

In step S302, an access request of health information is issued to the decentralized database based on the user identification. The access device may issue an access request to a distributed system, such as a block chain. The decentralized database identifies and authorizes the user identification based on an authorization file corresponding to the health information recorded in the decentralized database, and ratifies the access request and provides an instruction after identifying and authorizing the user identification. The decentralized database identifies and authorizes the user identification by identifying if the user identification matches an authorization object in the authorization file or if time when the access request is issued matches the authorization time of the authorization file.

In step S303, the encrypted health information is captured from the access space of the centralized database based on the instruction provided by the decentralized database. The centralized database can use the public key corresponding to the authorization file recorded in the decentralized database to encrypt the health information corresponding to the authorization file stored in the centralized database and store the encrypted health information in the access space. The decentralized database can provide an access address of the access space as the instruction.

In step S304, the private key corresponding to the user identification is used to decrypt the encrypted health information to obtain the health information. The user identification includes a pair of corresponding public key and private key, wherein the public key corresponds to the authorization object in the authorization file, and the private key corresponds to the user identification. That the user identification is identified and authorized successfully indicates that the user identification is the authorization object in the authorization file and the time when the access request is issued matches the authorization time in the authorization file. Therefore, the access device can acquire the encrypted health information from the access space based on the instruction, and use the private key to decrypt the encrypted health information encrypted by the public key.

Figure 4:
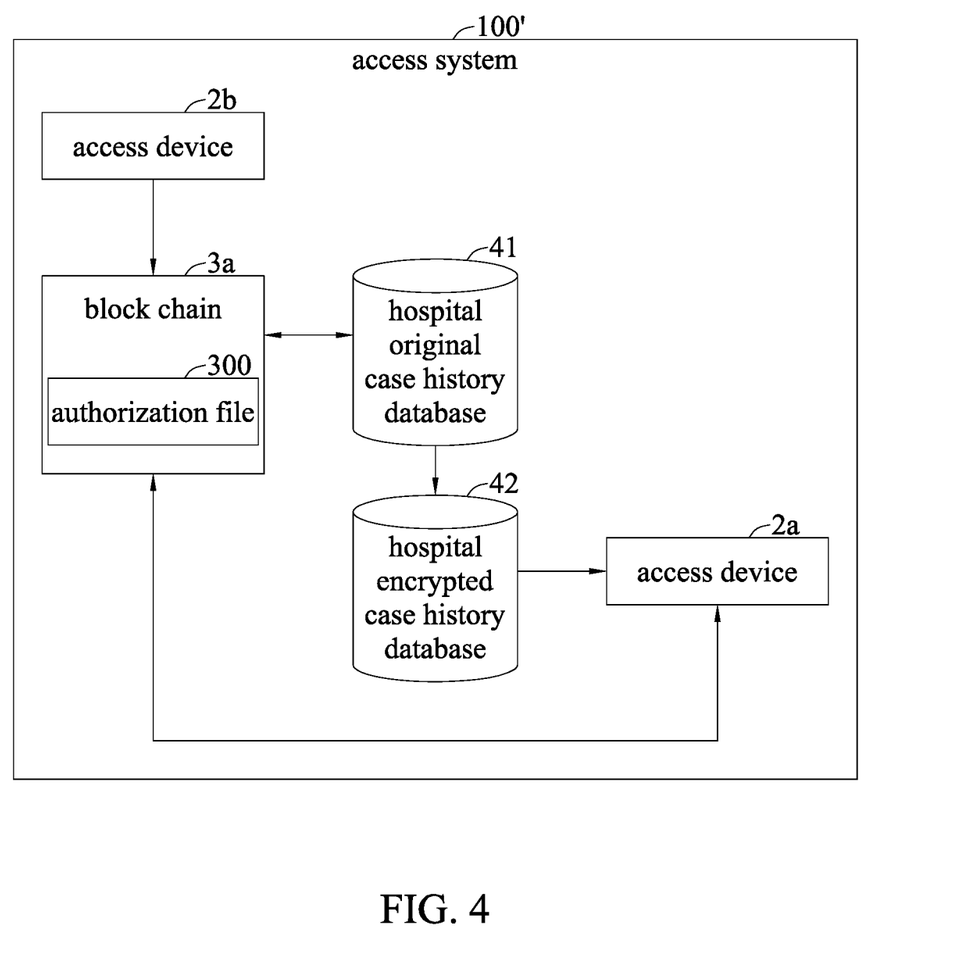
FIG. 4 is a schematic diagram of an access system for accessing health information of an embodiment according to the present disclosure.
Figure 5:
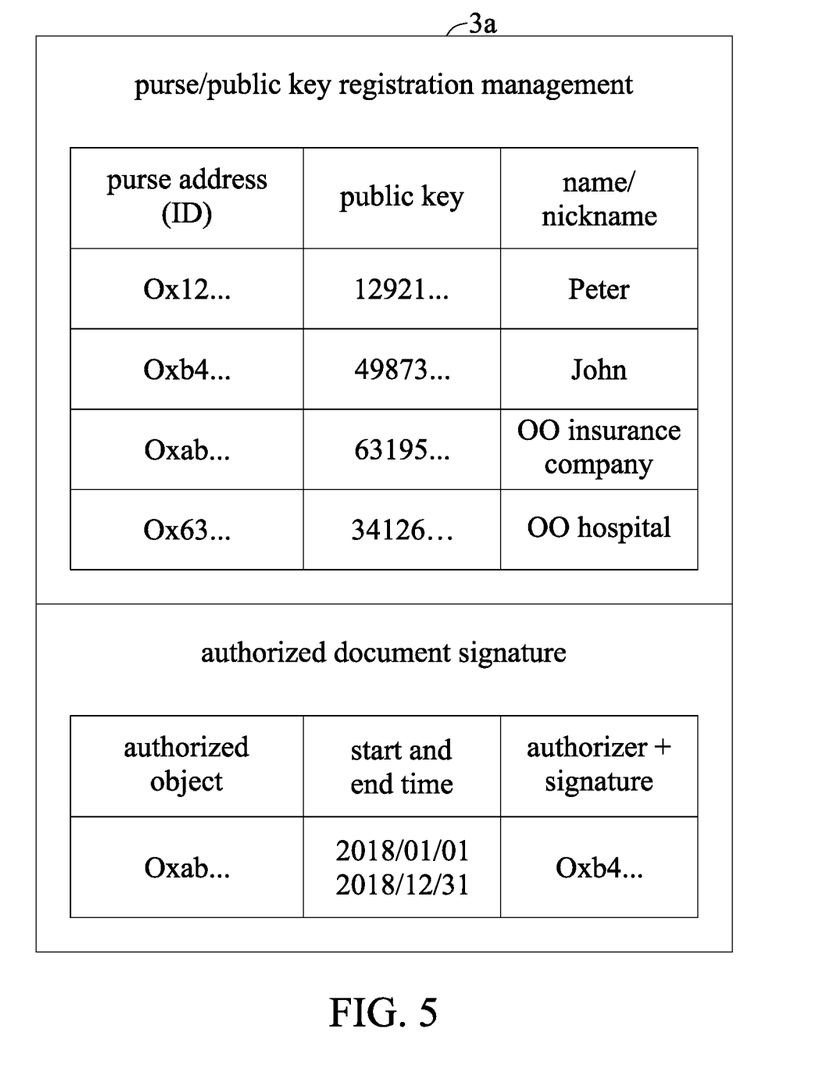
FIG. 5 is a schematic diagram of a block chain of an access system for accessing health information of an embodiment according to the present disclosure.
Figure 6:
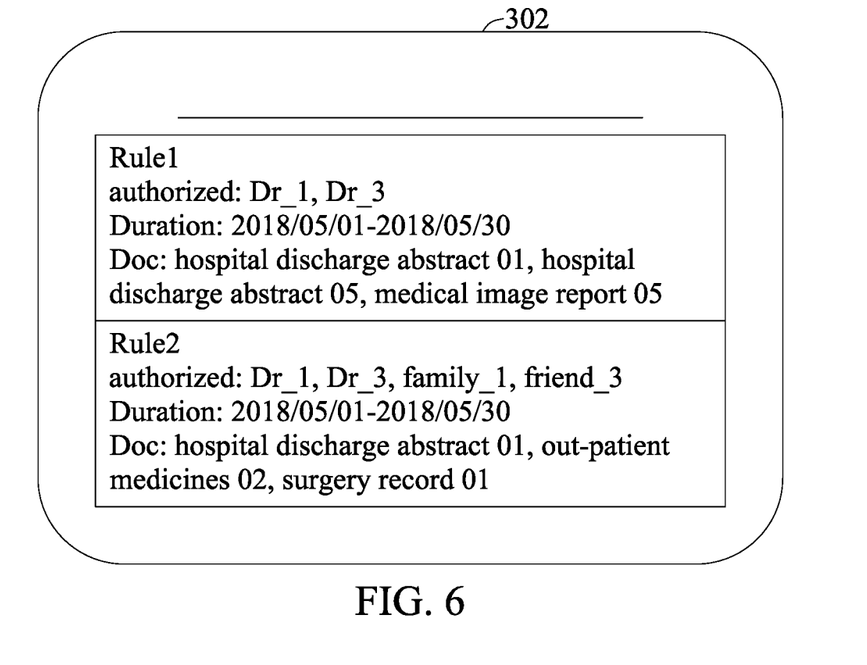
FIG. 6 is a schematic diagram of an authorization file of an access system for accessing health information of an embodiment according to the present disclosure.
Figure 7:
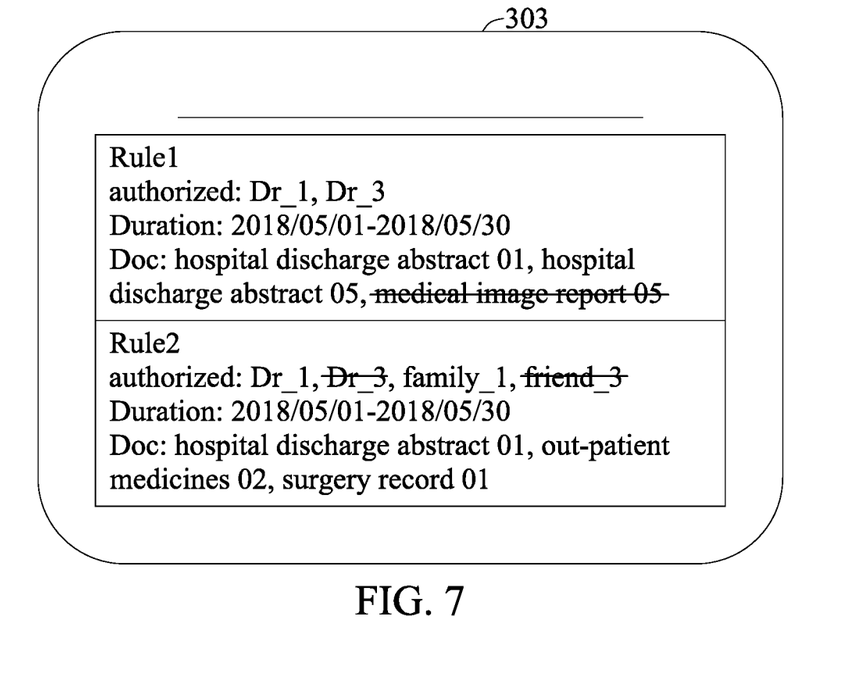
FIG. 7 is a schematic diagram of an authorization file of an access system for accessing health information of another embodiment according to the present disclosure.

Refer to FIGS. 4-6. FIG. 4 shows an access system 100' of another embodiment according to the present disclosure. The access system 100' comprises access devices 2*a* and 2*b*, a block chain 3*a*, a hospital original case history database 41 and a hospital encrypted case history database 42. FIG. 5 shows the block chain 3*a* of an embodiment according to the present disclosure. FIGS. 6 and 7 show authorization files 302 and 303 of an embodiment according to the present disclosure, respectively.

The patients or insurance policy holders can use the access device 2*b* to sign or change the authorization file 300 on the block chain 3*a*. As shown in FIG. 5, the records of the block chain 3*a* are divided into two parts, i.e., purse/public key registration management and authorization file signature. The purse/public key registration management includes a purse address (ID), a public key, and name/nickname. The authorization file includes an authorization object, start and end time, and authorization signature. The authorization file is signed as shown in FIG. 6. The authorization file 302 includes an authorization object (e.g., Dr_1 and Dr_3), authorization time (duration) (e.g., 2018/05/01-2018/05/30), and an authorization content (e.g., a hospital discharge abstract 01, a hospital discharge abstract 05, and a medical image report 05), which are rule 1. In rule 2, the authorization object is Dr_1, Dr_3, family_1 and friend_3, the authorization time (duration) is 2018/05/01-2018/05/30, and the authorization content is the hospital discharge abstract 01, an out-patient medicine 02 and a surgery report 01. Therefore, a patient or an insurance policy holder can set a variety of rules in the signed authorization file, and these rules can be applied to different authorization objects. For instance, family_1 and friend_3 can read the hospital discharge abstract, but cannot read the medical image report 05. The authorization file is changed as shown in FIG. 7. The medical image report 05 in the rule 1 of the authorization file 303 is deleted, and Dr_3 and friend_3 in rule 2 are deleted.

It is known from FIG. 5 that the block chain 3a records an authorization file signed by an insurance policy holder John (purse address Oxb4), wherein an object to whom is authorized is an OO insurance company has a purse address of Oxab. Therefore, the hospital original case history database 41 uses the public key of the OO insurance company to encrypt and store John' case history data into the hospital encrypted case history database 42. The OO insurance company uses the access device 2a to provide an access request of John's case history data on the block chain 3a. Then, the block chain 3a identifies if the authorization object in the authorization file signed by John is the OO insurance company, and, if so, ratifies the access request and instructs the access address of John's case history data, or does not ratify the access request. The block chain 3a ratifies the access request and provides the address of the hospital encrypted case history database 42, for the OO insurance company to use the access device 2a to acquire John's encrypted case history data from the hospital encrypted case history database 42, and use the OO insurance company's own private key to decrypt John's encrypted case history data to obtain John's case history data. In other words, the access devices 2a and 2b act as nodes on the block chain 3a. A user (may be a doctor, a patient/insurance policy holder, an OO insurance company, or an OO hospital) registers on the block chain 3a and obtains a purse address and a pair of corresponding public key and private key, wherein the public key is recorded on the block chain 3a, and the private key is acquired by its own access device 2a or 2b identifying the user identification. Therefore, the access device 2a or 2b can use the private key corresponding to the user identification to decrypt the encrypted case history data that is encrypted by the public key of the authorization object.

In sum, an access system, an access device and an access method for accessing health information according to the present disclosure can be applied to patients/insurance policy holders, hospitals and insurance companies. The patients/insurance policy holders can use the access device to sign or change an authorization file on the block chain. Health information, such as case history data, are stored in an original case history database on each hospital. The hospital original case history database can use the public key recorded in the block chain to encrypt case history data and store the encrypted case history data in an encrypted case history database across hospitals. Therefore, other hospitals or insurance companies can use the access device to the block chain to provide an access request of case history data, acquire the encrypted case history data from the encrypted case history database across hospitals after the access request is identified, and use its own private key to decrypt the encrypted case history data. Therefore, the present disclosure can prevent the health information from being leaked, improve the flexibility and convenience for changing the authorization, and realize personal data confidentiality and real-time medical efficiency.

It will be apparent to those skilled in the art that various modifications and variations can be made to the disclosed embodiments. It is intended that the specification and examples be considered as exemplary only, with a true scope of the disclosure being indicated by the following claims and their equivalents.

What is claimed is:

1. An access device for accessing health information, comprising:
    a memory storing a set of instructions; and
    a processor configured to execute the set of instructions to cause the access device to perform:
        identifying user identification to obtain a private key corresponding to the user identification;
        issuing an access request of health information to a decentralized database based on the user identification;
        identifying and authorizing by the decentralized database the user identification based on a recorded authorization file corresponding to the health information, wherein the recorded authorization file comprises an authorization object and authorization time, and identifying and authorizing the user identification comprises matching the user identification with the authorization object or the authorization time;
        ratifying the access request of the health information;
        providing an instruction after identifying and authorizing the user identifications;
        acquiring encrypted health information from an access space of a centralized database based on the instruction; and
        using the private key to decrypt the encrypted health information to obtain the health information.

2. The access device of claim 1, further comprising a display configured for displaying the health information or a storage apparatus configured for storing the health information.

3. The access device of claim 1, wherein the user identification comprises a public key corresponding to the private key and the authorization object in the authorization file and recorded in the decentralized database, allowing the centralized database to use the public key to encrypt and store the health information into the access space of the centralized database, wherein the decentralized database identifies and authorizes the user identification by:
    identifying whether the user identification, based on which the access device is identified, matches the authorization object of the authorization file, or
    identifying whether time when the access device issues the access request matches the authorization time of the authorization file.

4. An access method for accessing health information, comprising:
    identifying user identification to obtain a private key corresponding to the user identification;
    issuing, based on the user identification, an access request of health information to a decentralized database;
    identifying and authorizing by the decentralized database the user identification based on an authorization file corresponding to the health information, wherein the recorded authorization file comprises an authorization object and authorization time, and the decentralized database identifies and authorizes the user identification by matching the user identification with the authorization object or the authorization time;
    ratifying the access request of the health information;
    providing an instruction after identifying and authorizing the user identification;

acquiring encrypted health information from an access space of a centralized database based on the instruction; and using the private key to decrypt the encrypted health information to obtain the health information.

5. The access method of claim 4, further comprising displaying or storing the health information.

6. The access method of claim 4, wherein the user identification comprises a public key corresponding to the private key and the authorization object in the authorization file and recorded in the decentralized database, allowing the centralized database to use the public key to encrypt and store the health information into the access space of the centralized database, wherein the decentralized database identifies and authorizes the user identification by:

identifying whether the user identification, based on which the access device is identified, matches the authorization object of the authorization file, or identifying whether time when the access device issues the access request matches the authorization time of the authorization file.

7. An access system for accessing health information, comprising:

a memory storing a set of instructions; and a processor configured to execute the set of instructions to cause the access system to perform:

recording by a decentralized database an authorization file corresponding to health information and a public key corresponding to the authorization file, wherein the authorization file comprises an authorization object and authorization time;

storing by the decentralized database the health information, and using the public key to encrypt the health information to store encrypted health information into an access space of the centralized database;

issuing by an access device an access request of the health information to the decentralized database based on user identification;

identifying and authorizing by the decentralized database the user identification of the access device based on the authorization file corresponding to the health information, wherein the decentralized database identifies and authorizes the user identification by matching the user identification with the authorization object or the authorization time;

ratifying the access request of the health information;

providing an instruction after identifying and authorizing the user identification; and capturing the encrypted health information from the access space based on the instruction.

8. The access system of claim 7, wherein the access device uses a private key corresponding to the user identification to decrypt the encrypted health information to obtain the health information.

9. The access system of claim 8, wherein the public key corresponds to the private key and the authorization object in the authorization file and is recorded in the decentralized database, and the private key is obtained by the access device identifying the user identification.

10. The access system of claim 9, wherein decentralized database identifies and authorizes the user identification by:

identifying whether the user identification, based on which the access device is identified, matches the authorization object of the authorization file, or identifying whether time when the access device issues the access request matches the authorization time of the authorization file.

11. The access system of claim 7, wherein the centralized database searches the decentralized database for an authorization file corresponding to the health information periodically, and encrypts and stores the health information corresponding to the authorization file into the access space of the centralized database when the authorization file corresponding to the health information is in the decentralized database.

12. The access system of claim 7, wherein the decentralized database is a block chain, the centralized database is a hospital original case history database, and the access space is a hospital encrypted case history database.

13. The access system of claim 7, wherein the authorization file records an authorization object, authorization time and an authorization content, and the health information is a case history record including a case history number and case history data.

14. An access method for accessing health information, comprising:

recording an authorization file corresponding to health information and a public key corresponding to the authorization file in a decentralized database, wherein the authorization file comprises an authorization object and authorization time;

using the public key to encrypt the health information to store encrypted health information into an access space of a centralized database;

receiving an access request of the health information issued by an access device based on user identification;

identifying and authorizing the user identification of the access device based on the authorization file corresponding to the health information, wherein identifying and authorizing the user identification comprises matching the user identification with the authorization object or the authorization time;

ratifying the access request of the health information;

providing an instruction after the user identification is identified and authorized for the access device; and acquiring the encrypted health information from the access space based on the instruction.

15. The access method of claim 14, further comprising decrypting, by the access device using a private key corresponding to the user identification, the encrypted health information to acquire the health information.

16. The access method of claim 15, wherein the public key corresponds to the private key and the authorization object in the authorization file and is recorded in the decentralized database, and the private key is acquired by the access device identifying the user identification.

17. The access method of claim 16, wherein identifying and authorizing the user identification comprises:

identifying whether the user identification, based on which the access device is identified, matches the authorization object of the authorization file, or identifying whether time when the access device issues the access request matches the authorization time of the authorization file.

18. The access method of claim 14, further comprising searching, by the centralized database, the decentralized database for an authorization file corresponding to the health information periodically, and encrypting and storing the health information corresponding to the authorization file into the access space of the centralized database when the authorization file corresponding to the health information is in the decentralized database.

19. The access method of claim 14, wherein the decentralized database is a block chain, the centralized database is a hospital original case history database, and the access space is a hospital encrypted case history database.

20. The access method of claim 14, wherein the authorization file records an authorization object, authorization time and an authorization content, and the health information is a case history record including a case history number and a case history data.

\* \* \* \* \*